(12) United States Patent
Takei et al.

(10) Patent No.: US 10,088,486 B2
(45) Date of Patent: Oct. 2, 2018

(54) METHOD FOR DETECTING NEUROLOGICAL DISEASE ACCOMPANIED BY INFLAMMATION AND/OR DEMYELINATION

(71) Applicant: PUBLIC UNIVERSITY CORPORATION YOKOHAMA CITY UNIVERSITY, Yokohama-shi, Kanagawa (JP)

(72) Inventors: Kohtaro Takei, Yokohama (JP); Keita Takahashi, Kanagawa (JP); Yume Suzuki, Yokohama (JP); Yoshio Goshima, Yokohama (JP)

(73) Assignee: PUBLIC UNIVERSITY CORPORATION YOKOHAMA CITY UNIVERSITY, Yokohama-shi (JP)

( * ) Notice: Subject to any disclaimer, the term of this patent is extended or adjusted under 35 U.S.C. 154(b) by 0 days.

(21) Appl. No.: 14/646,544

(22) PCT Filed: Nov. 21, 2013

(86) PCT No.: PCT/JP2013/081385
§ 371 (c)(1),
(2) Date: May 21, 2015

(87) PCT Pub. No.: WO2014/080979
PCT Pub. Date: May 30, 2014

(65) Prior Publication Data
US 2015/0293125 A1    Oct. 15, 2015

(30) Foreign Application Priority Data

Nov. 22, 2012 (JP) ................. 2012-256701

(51) Int. Cl.
*G01N 33/53* (2006.01)
*G01N 33/566* (2006.01)
*G01N 33/567* (2006.01)
*G01N 33/68* (2006.01)

(52) U.S. Cl.
CPC ..... *G01N 33/6896* (2013.01); *G01N 2333/78* (2013.01); *G01N 2800/285* (2013.01); *G01N 2800/2835* (2013.01); *G01N 2800/52* (2013.01); *G01N 2800/54* (2013.01); *G01N 2800/7095* (2013.01)

(58) Field of Classification Search
None
See application file for complete search history.

(56) References Cited

U.S. PATENT DOCUMENTS

2010/0081136 A1    4/2010  Golz et al.

FOREIGN PATENT DOCUMENTS

| EP | 2 642 292 A1 | 9/2013 |
| JP | 2008-189615 A | 8/2008 |
| JP | 2010-215618 A | 9/2010 |

OTHER PUBLICATIONS

Cohen et al., "A diagnostic index of active demyelination: myelin basic protein in cerebrospinal fluid", Annals of Neurology, vol. 8, No. 1, Jul. 1980, pp. 25-31. (Abstract Only).
International Search Report (Form PCT/ISA/210) and partial English translation thereof, dated Feb. 25, 2014, for International Application No. PCT/JP2013/081385.
Kurihara et al., "The carboxyl-terminal region of Crtac1B/LOTUS acts as a functional domain in endogenous antagonism to Nogo receptor-1", Biochemical and Biophysical Research Communications, vol. 418, No. 2, 2012 (Published online Jan. 18, 2012), pp. 390-395.
Lennon et al., "A serum autoantibody marker of neuromyelitis optica: distinction from multiple sclerosis", Lancet, vol. 364, No. 9451, Dec. 11-17, 2004, pp. 2106-2112. (Abstract Only).
Polman et al., "Diagnostic Criteria for Multiple Sclerosis: 2010 Revisions to the McDonald Criteria", Annals of Neurology, vol. 69, No. 2, Feb. 2011, pp. 292-302.
Takahashi et al., Presentation Poster "LOTUS as a new biomarker for Multiple Sclerosis", Jun. 21, 2013 (Day 2), Neuro2013 (The 36th Annual Meeting of the Japan Neuroscience Society).

*Primary Examiner* — Olga N Chernyshev
(74) *Attorney, Agent, or Firm* — Birch, Stewart, Kolasch & Birch, LLP

(57) ABSTRACT

Novel means useful for definitive diagnosis of a neurological disease accompanied by at least one of inflammation and demyelination, such as multiple sclerosis or neuromyelitis optica, is disclosed. The method for detecting a neurological disease (excluding cerebral infarction) accompanied by at least one of inflammation and demyelination provided by the present invention comprises measuring Crtac1B protein in a sample separated from a subject. The presence of the neurological disease is detected based on a low value of the Crtac1B protein level.

10 Claims, 6 Drawing Sheets
Specification includes a Sequence Listing.

SEQUENCE LISTING

```
<160> NUMBER OF SEQ ID NOS: 3

<210> SEQ ID NO 1
<211> LENGTH: 2361
<212> TYPE: DNA
<213> ORGANISM: Homo sapiens
<220> FEATURE:
<221> NAME/KEY: CDS
<222> LOCATION: (357)..(2294)
<223> OTHER INFORMATION:

<400> SEQUENCE: 1
ctggctgccg gctgctgcca ccgcaatccc ggctcctaaa tcagcgcggg gaggcgctcc      60
ctccccacgc ccggctctcc gggctctcgg ggccgcgatt ggccgcgccg cgcccccca     120 ccccgggccc ccggctccag ctgccgcgcc attggctgcg ggcctccgcc agcctttaca    180
taagaccggg cgcgctcgag tggagttgta taaagcgagc gcgcggcgtc ggggcgggag    240
gctcgaggcc agcccgggac cggggctggg agcaagcagg cggcggcgcc ggcggcagag    300
gcggcagcga gcgcccgctt cccacgcccc taggcggcgg ggccgagagc gggagg atg    359
                                                                 Met
                                                                  1 gct ccg agc gct gac ccc ggc atg tcc agg atg tta ccg ttc ctg ctg      407
Ala Pro Ser Ala Asp Pro Gly Met Ser Arg Met Leu Pro Phe Leu Leu
          5                  10                  15 ctg ctc tgg ttt ctg ccc atc act gag ggg tcc cag cgg gct gaa ccc      455
Leu Leu Trp Phe Leu Pro Ile Thr Glu Gly Ser Gln Arg Ala Glu Pro
 20                  25                  30 atg ttc act gca gtc acc aac tca gtt ctg cct cct gac tat gac agt      503
Met Phe Thr Ala Val Thr Asn Ser Val Leu Pro Pro Asp Tyr Asp Ser
 35                  40                  45 aat ccc acc cag ctc aac tat ggt gtg gca gtt act gat gtg gac cat      551
Asn Pro Thr Gln Leu Asn Tyr Gly Val Ala Val Thr Asp Val Asp His
 50                  55                  60                  65 gat ggg gac ttt gag atc gtc gtg gcg ggg tac aat gga ccc aac ctg      599
Asp Gly Asp Phe Glu Ile Val Val Ala Gly Tyr Asn Gly Pro Asn Leu
                 70                  75                  80 gtt ctg aag tat gac cgg gcc cag aag cgg ctg gtg aac atc gcg gtc      647
Val Leu Lys Tyr Asp Arg Ala Gln Lys Arg Leu Val Asn Ile Ala Val
         85                  90                  95 gat gag cgc agc tca ccc tac tac gcg ctg cgg gac cgg cag ggg aac      695
Asp Glu Arg Ser Ser Pro Tyr Tyr Ala Leu Arg Asp Arg Gln Gly Asn
             100                 105                 110 gcc atc ggg gtc aca gcc tgc gac atc gac ggg gac ggc cgg gag gag      743
Ala Ile Gly Val Thr Ala Cys Asp Ile Asp Gly Asp Gly Arg Glu Glu
        115                 120                 125 atc tac ttc ctc aac acc aat aat gcc ttc tcg ggg gtg gcc acg tac      791
Ile Tyr Phe Leu Asn Thr Asn Asn Ala Phe Ser Gly Val Ala Thr Tyr
```

```
       130                 135                 140                 145
  acc gac aag ttg ttc aag ttc cgc aat aac cgg tgg gaa gac atc ctg      839
  Thr Asp Lys Leu Phe Lys Phe Arg Asn Asn Arg Trp Glu Asp Ile Leu
                      150                 155                 160 agc gat gag gtc aac gtg gcc cgt ggt gtg gcc agc ctc ttt gcc gga      887
  Ser Asp Glu Val Asn Val Ala Arg Gly Val Ala Ser Leu Phe Ala Gly
              165                 170                 175 cgc tct gtg gcc tgt gtg gac aga aag ggc tct gga cgc tac tct atc      935
  Arg Ser Val Ala Cys Val Asp Arg Lys Gly Ser Gly Arg Tyr Ser Ile
          180                 185                 190 tac att gcc aat tac gcc tac ggt aat gtg ggc cct gat gcc ctc att      983
  Tyr Ile Ala Asn Tyr Ala Tyr Gly Asn Val Gly Pro Asp Ala Leu Ile
      195                 200                 205 gaa atg gac cct gag gcc agt gac ctc tcc cgg ggc att ctg gcg ctc     1031
  Glu Met Asp Pro Glu Ala Ser Asp Leu Ser Arg Gly Ile Leu Ala Leu
  210                 215                 220                 225 aga gat gtg gct gct gag gct ggg gtc agc aaa tat aca ggg ggc cga     1079
  Arg Asp Val Ala Ala Glu Ala Gly Val Ser Lys Tyr Thr Gly Gly Arg
                  230                 235                 240 ggc gtc agc gtg ggc ccc atc ctc agc agc agt gcc tcg gat atc ttc     1127
  Gly Val Ser Val Gly Pro Ile Leu Ser Ser Ser Ala Ser Asp Ile Phe
              245                 250                 255 tgc gac aat gag aat ggg cct aac ttc ctt ttc cac aac cgg ggc gat     1175
  Cys Asp Asn Glu Asn Gly Pro Asn Phe Leu Phe His Asn Arg Gly Asp
          260                 265                 270 ggc acc ttt gtg gac gct gcg gcc agt gct ggt gtg gac gac ccc cac     1223
  Gly Thr Phe Val Asp Ala Ala Ala Ser Ala Gly Val Asp Asp Pro His
      275                 280                 285 cag cat ggg cga ggt gtc gcc ctg gct gac ttc aac cgt gat ggc aaa     1271
  Gln His Gly Arg Gly Val Ala Leu Ala Asp Phe Asn Arg Asp Gly Lys
  290                 295                 300                 305 gtg gac atc gtc tat ggc aac tgg aat ggc ccc cac cgc ctc tat ctg     1319
  Val Asp Ile Val Tyr Gly Asn Trp Asn Gly Pro His Arg Leu Tyr Leu
                  310                 315                 320 caa atg agc acc cat ggg aag gtc cgc ttc cgg gac atc gcc tca ccc     1367
  Gln Met Ser Thr His Gly Lys Val Arg Phe Arg Asp Ile Ala Ser Pro
              325                 330                 335 aag ttc tcc atg ccc tcc cct gtc cgc acg gtc atc acc gcc gac ttt     1415
  Lys Phe Ser Met Pro Ser Pro Val Arg Thr Val Ile Thr Ala Asp Phe
          340                 345                 350 gac aat gac cag gag ctg gag atc ttc ttc aac aac att gcc tac cgc     1463
  Asp Asn Asp Gln Glu Leu Glu Ile Phe Phe Asn Asn Ile Ala Tyr Arg
      355                 360                 365 agc tcc tca gcc aac cgc ctc ttc cgc gtc atc cgt aga gag cac gga     1511
  Ser Ser Ser Ala Asn Arg Leu Phe Arg Val Ile Arg Arg Glu His Gly
  370                 375                 380                 385 gac ccc ctc atc gag gag ctc aat ccc ggc gac gcc ttg gag cct gag     1559
  Asp Pro Leu Ile Glu Glu Leu Asn Pro Gly Asp Ala Leu Glu Pro Glu
                  390                 395                 400 ggc cgg ggc aca ggg ggt gtg gtg acc gac ttc gac gga gac ggg atg     1607
  Gly Arg Gly Thr Gly Gly Val Val Thr Asp Phe Asp Gly Asp Gly Met
              405                 410                 415 ctg gac ctc atc ttg tcc cat gga gag tcc atg gct cag ccg ctg tcc     1655
  Leu Asp Leu Ile Leu Ser His Gly Glu Ser Met Ala Gln Pro Leu Ser
          420                 425                 430 gtc ttc cgg ggc aat cag ggc ttc aac aac aac tgg ctg cga gtg gtg     1703
  Val Phe Arg Gly Asn Gln Gly Phe Asn Asn Asn Trp Leu Arg Val Val
      435                 440                 445 cca cgc acc cgg ttt ggg gcc ttt gcc agg gga gct aag gtc gtg ctc     1751
```

```
                    Pro Arg Thr Arg Phe Gly Ala Phe Ala Arg Gly Ala Lys Val Val Leu
                    450             455                 460                 465 tac acc aag aag agt ggg gcc cac ctg agg atc atc gac ggg ggc tca                    1799
Tyr Thr Lys Lys Ser Gly Ala His Leu Arg Ile Ile Asp Gly Gly Ser
                    470                 475                 480 ggc tac ctg tgt gag atg gag ccc gtg gca cac ttt ggc ctg ggg aag                    1847
Gly Tyr Leu Cys Glu Met Glu Pro Val Ala His Phe Gly Leu Gly Lys
                485                 490                 495 gat gaa gcc agc agt gtg gag gtg acg tgg cca gat ggc aag atg gtg                    1895
Asp Glu Ala Ser Ser Val Glu Val Thr Trp Pro Asp Gly Lys Met Val
            500                 505                 510 agc cgg aac gtg gcc agc ggg gag atg aac tca gtg ctg gag atc ctc                    1943
Ser Arg Asn Val Ala Ser Gly Glu Met Asn Ser Val Leu Glu Ile Leu
        515                 520                 525 tac ccc cgg gat gag gac aca ctt cag gac cca gcc cca ctg gag tgt                    1991
Tyr Pro Arg Asp Glu Asp Thr Leu Gln Asp Pro Ala Pro Leu Glu Cys
530                 535                 540                 545 ggc caa gga ttc tcc cag cag gaa aat ggc cat tgc atg gac acc aat                    2039
Gly Gln Gly Phe Ser Gln Gln Glu Asn Gly His Cys Met Asp Thr Asn
                550                 555                 560 gaa tgc atc cag ttc cca ttc gtg tgc cct cga gac aag ccc gta tgt                    2087
Glu Cys Ile Gln Phe Pro Phe Val Cys Pro Arg Asp Lys Pro Val Cys
            565                 570                 575 gtc aac acc tat gga agc tac agg tgc cgg acc aac aag aag tgc agt                    2135
Val Asn Thr Tyr Gly Ser Tyr Arg Cys Arg Thr Asn Lys Lys Cys Ser
        580                 585                 590 cgg ggc tac gag ccc aac gag gat ggc aca gcc tgc gtg gct caa gtg                    2183
Arg Gly Tyr Glu Pro Asn Glu Asp Gly Thr Ala Cys Val Ala Gln Val
595                 600                 605 gcc ttt tta ggt ggg tat tct tca gcc gcc tct aga atc tct gag cct                    2231
Ala Phe Leu Gly Gly Tyr Ser Ser Ala Ala Ser Arg Ile Ser Glu Pro
610                 615                 620                 625 ctc tct cgg gcc tca tat ctt tct cta ggc ctt gga ctt tgc ctt cag                    2279
Leu Ser Arg Ala Ser Tyr Leu Ser Leu Gly Leu Gly Leu Cys Leu Gln
                630                 635                 640 tta tat gca ctt taa atcccatcaa taaggaaaaa acaaaacaa  aactaacagc                    2334
Leu Tyr Ala Leu
            645 ctttgtggaa aactaaaaaa aaaaaaa                                                      2361

<210> SEQ ID NO 2
<211> LENGTH: 645
<212> TYPE: PRT
<213> ORGANISM: Homo sapiens

<400> SEQUENCE: 2

Met Ala Pro Ser Ala Asp Pro Gly Met Ser Arg Met Leu Pro Phe Leu
1               5                   10                  15

Leu Leu Leu Trp Phe Leu Pro Ile Thr Glu Gly Ser Gln Arg Ala Glu
            20                  25                  30

Pro Met Phe Thr Ala Val Thr Asn Ser Val Leu Pro Pro Asp Tyr Asp
        35                  40                  45

Ser Asn Pro Thr Gln Leu Asn Tyr Gly Val Ala Val Thr Asp Val Asp
    50                  55                  60

His Asp Gly Asp Phe Glu Ile Val Val Ala Gly Tyr Asn Gly Pro Asn
65                  70                  75                  80

Leu Val Leu Lys Tyr Asp Arg Ala Gln Lys Arg Leu Val Asn Ile Ala
                85                  90                  95
```

```
Val Asp Glu Arg Ser Ser Pro Tyr Tyr Ala Leu Arg Asp Arg Gln Gly
            100                 105                 110

Asn Ala Ile Gly Val Thr Ala Cys Asp Ile Asp Gly Asp Gly Arg Glu
            115                 120                 125

Glu Ile Tyr Phe Leu Asn Thr Asn Asn Ala Phe Ser Gly Val Ala Thr
        130                 135                 140

Tyr Thr Asp Lys Leu Phe Lys Phe Arg Asn Asn Arg Trp Glu Asp Ile
145                 150                 155                 160

Leu Ser Asp Glu Val Asn Val Ala Arg Gly Val Ala Ser Leu Phe Ala
                165                 170                 175

Gly Arg Ser Val Ala Cys Val Asp Arg Lys Gly Ser Gly Arg Tyr Ser
            180                 185                 190

Ile Tyr Ile Ala Asn Tyr Ala Tyr Gly Asn Val Gly Pro Asp Ala Leu
        195                 200                 205

Ile Glu Met Asp Pro Glu Ala Ser Asp Leu Ser Arg Gly Ile Leu Ala
        210                 215                 220

Leu Arg Asp Val Ala Ala Glu Ala Gly Val Ser Lys Tyr Thr Gly Gly
225                 230                 235                 240

Arg Gly Val Ser Val Gly Pro Ile Leu Ser Ser Ala Ser Asp Ile
            245                 250                 255

Phe Cys Asp Asn Glu Asn Gly Pro Asn Phe Leu Phe His Asn Arg Gly
            260                 265                 270

Asp Gly Thr Phe Val Asp Ala Ala Ser Ala Gly Val Asp Asp Pro
            275                 280                 285

His Gln His Gly Arg Gly Val Ala Leu Ala Asp Phe Asn Arg Asp Gly
    290                 295                 300

Lys Val Asp Ile Val Tyr Gly Asn Trp Asn Gly Pro His Arg Leu Tyr
305                 310                 315                 320

Leu Gln Met Ser Thr His Gly Lys Val Arg Phe Arg Asp Ile Ala Ser
                325                 330                 335

Pro Lys Phe Ser Met Pro Ser Pro Val Arg Thr Val Ile Thr Ala Asp
            340                 345                 350

Phe Asp Asn Asp Gln Glu Leu Glu Ile Phe Phe Asn Asn Ile Ala Tyr
        355                 360                 365

Arg Ser Ser Ser Ala Asn Arg Leu Phe Arg Val Ile Arg Arg Glu His
370                 375                 380

Gly Asp Pro Leu Ile Glu Glu Leu Asn Pro Gly Asp Ala Leu Glu Pro
385                 390                 395                 400

Glu Gly Arg Gly Thr Gly Gly Val Val Thr Asp Phe Asp Gly Asp Gly
                405                 410                 415

Met Leu Asp Leu Ile Leu Ser His Gly Glu Ser Met Ala Gln Pro Leu
            420                 425                 430

Ser Val Phe Arg Gly Asn Gln Gly Phe Asn Asn Asn Trp Leu Arg Val
        435                 440                 445

Val Pro Arg Thr Arg Phe Gly Ala Phe Ala Arg Gly Ala Lys Val Val
    450                 455                 460

Leu Tyr Thr Lys Lys Ser Gly Ala His Leu Arg Ile Ile Asp Gly Gly
465                 470                 475                 480

Ser Gly Tyr Leu Cys Glu Met Glu Pro Val Ala His Phe Gly Leu Gly
                485                 490                 495

Lys Asp Glu Ala Ser Ser Val Gly Val Thr Trp Pro Asp Gly Lys Met
            500                 505                 510

Val Ser Arg Asn Val Ala Ser Gly Glu Met Asn Ser Val Leu Glu Ile
```

```
                515                 520                 525
Leu Tyr Pro Arg Asp Glu Asp Thr Leu Gln Asp Pro Ala Pro Leu Glu
        530                 535                 540

Cys Gly Gln Gly Phe Ser Gln Gln Glu Asn Gly His Cys Met Asp Thr
545                 550                 555                 560

Asn Glu Cys Ile Gln Phe Pro Phe Val Cys Pro Arg Asp Lys Pro Val
                565                 570                 575

Cys Val Asn Thr Tyr Gly Ser Tyr Arg Cys Arg Thr Asn Lys Lys Cys
            580                 585                 590

Ser Arg Gly Tyr Glu Pro Asn Glu Asp Gly Thr Ala Cys Val Ala Gln
        595                 600                 605

Val Ala Phe Leu Gly Gly Tyr Ser Ser Ala Ala Ser Arg Ile Ser Glu
    610                 615                 620

Pro Leu Ser Arg Ala Ser Tyr Leu Ser Leu Gly Leu Gly Leu Cys Leu
625                 630                 635                 640

Gln Leu Tyr Ala Leu
                645

<210> SEQ ID NO 3
<211> LENGTH: 31
<212> TYPE: PRT
<213> ORGANISM: Mus musculus

<400> SEQUENCE: 3

Arg Ser Val Ala Ser Glu Glu Met Asn Ser Val Leu Glu Ile Leu Tyr
1               5                   10                  15

Pro Gln Asp Glu Asp Lys Leu Gln Asn Thr Ala Pro Leu Glu Cys
            20                  25                  30
```

METHOD FOR DETECTING NEUROLOGICAL DISEASE ACCOMPANIED BY INFLAMMATION AND/OR DEMYELINATION

TECHNICAL FIELD

The present invention relates to a method for detecting a neurological disease accompanied by at least one of inflammation and demyelination.

BACKGROUND ART

As markers for definitive diagnosis of multiple sclerosis (MS), oligoclonal bands detected in cerebrospinal fluid, and the IgG index for evaluation of quantitative IgG changes in serum and spinal fluid, are used at present. However, these markers are not MS-specific, and patients clinically diagnosed with MS are negative for the markers in many cases. Therefore, a sufficient diagnosis cannot be made by using these markers only (Non-patent Document 1). A high serum antibody titer of anti-aquaporin 4 antibody in patients with neuromyelitis optica (NMO: which is currently recognized as the different disease from MS) (Non-patent Document 2), which was previously included in MS, is also available as a disease state-associated marker. However, NMO is regarded as different disease at present. Moreover, some patients without detection of the above-mentioned antibody meet diagnostic criteria for NMO, others with detection of it cannot meet the criteria. Thus, diagnosis by comprehensive judgment with an additional diagnostic marker(s) is strongly demanded. In addition to the above markers, MRI findings are taken into account for differential diagnosis of multiple sclerosis and neuromyelitis optica. The presence of cells (monocytes, polymorphonuclear leukocytes and the like) in cerebrospinal fluid, a low glucose level (in bacterial, tuberculous and fungal meningitis and the like) and the like are main criteria for meningitis, meningoencephalitis, encephalitis and encephalopathy, but these examination findings are often not obvious in meningitis, meningoencephalitis, encephalitis and encephalopathy. Moreover, there is no molecular marker available for the diagnosis.

In many cases of multiple sclerosis and neuromyelitis optica, exacerbation of functional impairment proceeds while relapse and remission are repeated after definitive diagnosis, or, in some cases, the disease activity is increased without remission, causing continuous exacerbation of functional impairment. In the acute management of these diseases, it is primarily important to evaluate and diagnose the disease states and provide treatment as soon as possible to prevent exacerbation of the functional impairment during acute relapse or increased disease activity. The disease activity is commonly evaluated using MRI. However, facilities where MRI scan is available are limited, and, even among such facilities, there are only a more limited number of facilities where the scan can be carried out emergently. Besides MRI, detection of myelin basic protein (MBP) in the spinal fluid is sometimes used for the diagnosis of relapse (Non-patent Document 3), but the sufficient diagnosis cannot be made by using it because it lacks specificity. There is no objective indicator for diagnosing the disease condition of meningitis.

Patent Document 1 describes a method in which a low level of plasma Crtac1 protein is used as an indicator for detection of cerebral infarction or identification of the type of cerebral infarction. However, the document does not disclose at all a method for early definitive diagnosis of a neurological disease accompanied by at least one of inflammation and demyelination, such as multiple sclerosis.

PRIOR ART DOCUMENT(S)

Patent Document(s)

Patent Document 1: WO 2012/067151

Non-Patent Document(s)

Non-patent Document 1: Chris H. Polman et al., Ann Neurol 69: 292-302, 2011
Non-patent Document 2: Lennon V A et al., Lancet 364: 2106-2112, 2004
Non-patent Document 3: Cohen S R et al. Ann Neurol 8: 25-31, 1980

SUMMARY OF THE INVENTION

Problems to be Solved by the Invention

Accordingly, an object of the present invention is to provide novel means useful for definitive diagnosis of a neurological disease accompanied by at least one of inflammation and demyelination, such as multiple sclerosis or neuromyelitis optica.

Means for Solving the Problems

As a result of intensive study, the present inventors discovered that the level of Crtac1B protein was significantly lowered in patients with relapse of multiple sclerosis than in the normal controls; that the Crtac1B protein level was similarly lowered in neuromyelitis optica, Guillain-Barrésyndrome, chronic inflammatory demyelinating polyneuropathy, meningitis/meningoencephalitis, and neurosarcoidosis; and that a low value of the Crtac1B protein level can be used as an indicator for detecting such neurological diseases accompanied by at least one of inflammation and demyelination, thereby completing the present invention.

That is, the present invention provides a method for detecting a neurological disease (excluding cerebral infarction) accompanied by at least one of inflammation and demyelination, the method comprising measuring Crtac1B protein in a sample separated from a subject, wherein the presence of the neurological disease is detected by a low value of the Crtac1B protein level.

Effect of the Invention

The present invention provides a novel objective indicator useful for definitive diagnosis of neurological diseases accompanied by at least one of inflammation and demyelination, such as multiple sclerosis. A patient accompanied by a decrease in Crtac1B can be judged to be highly likely to be suffering from a neurological disease accompanied by at least one of inflammation and demyelination even in cases where the patient is negative for a conventional diagnostic indicator, for example, cases where the patient is negative for oligoclonal bands or cases where the IgG index is normal. Thus, the diagnostic error can be largely decreased. Facilities where MRI scan is available are limited, but measurement of Crtac1B protein level in a sample derived from a subject can be easily carried out without requiring a large-scale apparatus. Thus, the measurement is a useful test which can be commonly and widely carried out. According to the correlation between changes in Crtac1B and the disease state revealed by the present inventors, a low level of Crtac1B can be an important objective indicator for evaluation of a therapeutic effect on, or the progress of, a neurological disease accompanied by at least one of inflammation and demyelination. The new objective indicator provided by the present invention, a low Crtac1B level, can be a useful indicator for aiding physicians in diagnosing the development, relapse, progress and the like of a neurological disease accompanied by at least one of inflammation and demyelination.

MODE FOR CARRYING OUT THE INVENTION

Figure 1:
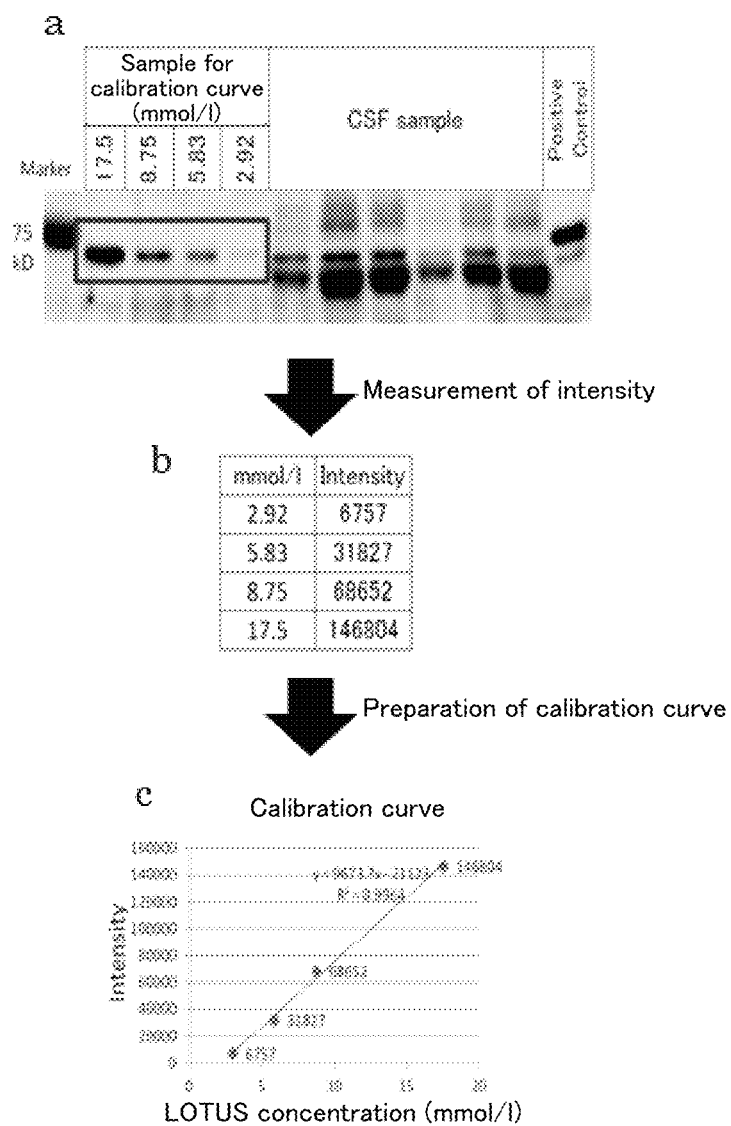
FIG. 1 is a diagram illustrating the method for preparing a calibration curve in Examples.

The "neurological disease accompanied by at least one of inflammation and demyelination" to be detected in the present invention is a neurological disease (excluding cerebral infarction) in which inflammation, demyelination, or both of these occur at any of the stages of the disease, typically at an early stage after the onset. Specific examples of such a neurological disease include demyelinating disease in central nervous system such as multiple sclerosis and neuromyelitis optica; inflammatory disease in central nervous system such as meningitis, meningoencephalitis, encephalitis, and encephalopathy; peripheral demyelinating neuropathies such as Guillain-Barré syndrome and chronic inflammatory demyelinating polyneuropathy; and acute central nervous system disorders complicating autoimmune diseases, such as neurosarcoidosis. Meningitis, meningoencephalitis, encephalitis and encephalopathy occur due to various causes such as pathogen infection, infiltration of cancer into the central nervous system, autoimmunity and metabolic disorders. In the present invention, examples of these diseases include all types of meningitis, meningoencephalitis, encephalitis and encephalopathy, irrespective of what the causes of these diseases are, and examples of their causes include viral, bacterial, tuberculous, fungal, carcinomatous, autoimmune, and metabolic causes. Neurological diseases classified into the neurodegenerative diseases (for example, amyotrophic lateral sclerosis and multiple system atrophy) are neurological diseases in which neither inflammation nor demyelination occurs, and not included in the "neurological disease accompanied by at least one of inflammation and demyelination" to be detected in the present invention.

The cartilage acidic protein 1 (Crtac1) gene (NCBI Gene database, Gene ID: 55118), which encodes Crtac1B protein, is known to have two transcript variants, Crtac1A and Crtac1B, and these variants are deposited in NCBI GenBank under Accession Nos. NM_018058 (NP 060528.3 for the protein) and NM_001206528 (NP_001193457.1 for the protein), respectively. SEQ ID NOs:1 and 2 in SEQUENCE LISTING show the Crtac1B gene sequence deposited as NM_001206528 (NP 001193457.1) and the amino acid sequence encoded thereby. The region corresponding to the 1st to 606th amino acids is identical between Crtac1A protein and Crtac1B protein, and this region is followed by a region characteristic to each variant. It should be noted that the sequences deposited in GenBank described above are mere examples of wild-type sequences, and there may be naturally-occurring Crtac1B proteins having the same amino acid sequence as described above except that a small number of (for example, 1 to several) amino acids are substituted, deleted, inserted, and/or added as a result of gene sequence polymorphism and/or the like. The Crtac1B referred to in the present invention also includes such naturally-occurring mutants.

In the present invention, the Crtac1B protein level in a sample separated from a subject is measured. Examples of samples which may be preferably used include blood samples (whole blood, serum, and plasma) and cerebrospinal fluid samples. Although cerebrospinal fluid samples are used in the following Examples, blood samples may also be used for carrying out the method of the present invention since cerebrospinal fluid flows into veins.

The method of analyzing the sample is not limited, and any method may be used as long as the method allows quantitative measurement of Crtac1B protein present in the sample. Examples of the analysis method include, but are not limited to, various well-established techniques such as mass spectrometry, chromatography (liquid chromatography, gas chromatography and the like), electrophoresis (capillary electrophoresis and the like), and immunoassays using an antibody; and methods using an aptamer instead of the antibody.

Examples of the mass spectrometry include Laser-Desorption/Ionization Time Of Flight/Mass Spectrometry (LDI-TOF/MS) and Electro-Spray Ionization Mass Spectrometry (ESI-MS). Analysis devices are commercially available for both methods, and the methods can be easily carried out by those skilled in the art.

Known immunoassays are classified into the sandwich method, competition method, agglutination method, Western blotting, etc. from the viewpoint of the reaction mode, or classified into radioimmunoassay, fluorescence immunoassay, enzyme immunoassay (EIA), biotin immunoassay, etc. from the viewpoint of the label employed. Any of these methods are included in the "immunoassay", and can be used for the measurement of Crtac1B protein. Specific examples of the immunoassay that may be used include, but are not limited to, ELISA, turbidimetric immunoassay (TIA method), latex immunoagglutination (LATEX method), electrochemiluminescence immunoassay (ECLIA method), and immunochromatography. The protein chip method, wherein a protein of interest is detected with an antibody immobilized on a glass or polymer substrate, can also be used.

Although either a polyclonal antibody or monoclonal antibody can be used in the immunoassay, a monoclonal antibody or its antigen-binding fragment is preferably used in view of reproducibility. In cases where Crtac1B protein is measured by an immunoassay in the present invention, a commercially available Crtac1 antibody may be used, or an antibody that binds to Crtac1B protein or its antigen-binding fragment may be prepared and used.

Methods for preparing an antibody and its antigen-binding fragment are well known, and, for example, the hybridoma method may be used for preparation of the antibody. More specifically, for example, Crtac1B protein or its fragment prepared by chemical synthesis or a genetic engineering method is used as an immunogen for immunization of an animal (excluding human) together with, if necessary, an adjuvant, to induce antibodies against Crtac1B in the body of the animal. Hybridomas can be prepared by collecting antibody-producing cells such as spleen cells or lymphocytes from the animal, and fusing the collected cells with immortalized cells such as myeloma cells. Using Crtac1B protein to be detected as a screening antigen, a hybridoma that specifically binds to Crtac1B protein is selected from the hybridomas. By allowing the selected hybridoma to grow, a monoclonal antibody against Crtac1B protein can be obtained from the culture supernatant. Since the amino acid sequence of Crtac1B protein and the base sequence encoding it are known as described above, those skilled in the art can easily prepare the Crtac1B protein or fragment thereof to be used as the immunogen by an ordinary method. Since, in the present invention, Crtac1B protein in a sample derived from a human subject is mainly measured, an immunogen prepared based on the amino acid sequence of human Crtac1B is usually used for the preparation of the antibody to be used in the immunoassay. However, as long as an antibody having binding capacity to the Crtac1B protein to be measured can be obtained, an immunogen prepared based on the amino acid sequence of Crtac1B of an animal species other than human, such as mouse, may be used.

The "antigen-binding fragment" may be any antibody fragment as long as the fragment retains binding capacity (antigen-antibody reactivity) to the corresponding antigen of the original antibody. Specific examples of the antigen-binding fragment include, but are not limited to, Fab, F(ab')$_2$, and scFv. As is well known, Fab and F(ab')$_2$ can be obtained by treating a monoclonal antibody with a protease such as papain or pepsin. Methods for preparing scFv (single chain fragment of variable region, single-chain antibody) are also well known. For example, mRNA of a hybridoma prepared as described above is extracted, and a single-stranded cDNA is prepared therefrom. PCR is carried out using primers specific to the H chain and the L chain of immunoglobulin to amplify the H-chain gene and the L-chain gene of the immunoglobulin, and these chains are linked together using a linker. After giving an appropriate restriction site thereto, the resultant is introduced into a plasmid vector. *E. coli* is then transformed with the vector, and allowed to express scFv. By recovering the expressed scFv from the *E. coli*, scFv can be obtained.

For simply and rapidly carrying out the immunoassay, the immunoassay is preferably carried out using an antibody that does not substantially bind to Crtac1A protein and is highly specific to Crtac1B protein, or an antigen-binding fragment of such an antibody. Such an antibody highly specific to Crtac1B protein (anti-Crtac1B antibody) can be obtained by, for example, preparing antibodies using as an immunogen the C-terminal region corresponding to the 607th and later amino acids, which is the region absent in Crtac1A and characteristic to Crtac1B, and using Crtac1A protein and Crtac1B protein as screening antigens to select an antibody that does not bind to Crtac1A but binds to Crtac1B. However, as described in the Examples below, in cases of a method with which the molecular weights of detected proteins can also be known such as Western blotting, Crtac1A and Crtac1B can be distinguished from each other based on the difference in the molecular weight, so that measurement of the Crtac1B level is possible even with an antibody that binds to both Crtac1A and Crtac1B.

Measurement by the sandwich method using an anti-Crtac1B antibody can be carried out, for example, as follows. An anti-Crtac1B antibody is immobilized on a solid support such as a plate or particles to provide an immobilized antibody. A labeling substance (enzyme, fluorescent substance, chemiluminescent substance, radioactive substance, or the like) is bound to an anti-Crtac1 antibody that binds to both Crtac1A and Crtac1B, to provide a labeled antibody. By bringing the immobilized antibody into contact with the sample, Crtac1B in the sample is allowed to specifically bind to the immobilized antibody. By this, the Crtac1B is captured on the support via the immobilized antibody. The support is then washed, and allowed to react with the labeled antibody. The support is then washed to remove unreacted labeled antibody, and the signal from the labeling substance is measured by an appropriate method. In cases where an enzyme is used as the labeling substance, a substrate such as a coloring substrate, fluorescent substrate or luminescent substrate corresponding to the enzyme may be allowed to react with the enzyme, and the resulting signal may be measured.

The method of detection of the signal is appropriately selected depending on the type of the labeling substance. For example, a colorimeter or spectrophotometer may be used in cases where the signal is coloration; a fluorometer may be used in cases where the signal is fluorescence; a photon counter may be used in cases where the signal is luminescence; and a radiation meter may be used in cases where the signal is radiation. Crtac1B in a sample can be quantified by subjecting standard samples containing Crtac1B at various known concentrations to an immunoassay to measure the Crtac1B levels, preparing a calibration curve by plotting the correlation between the amount of the signal from the labeling substance and the Crtac1B concentration in each standard sample, subjecting the sample containing Crtac1B at an unknown concentration to the same measurement operation to measure the amount of the signal from the label, and then applying the measured value to the calibration curve.

A method for measuring the Crtac1B level by Western blotting is as described in detail in the Examples below. Since Crtac1B is detected as a band having a molecular weight of 70 kD, an anti-Crtac1 antibody that also binds to Crtac1A may be used as the primary antibody. As the secondary antibody, an anti-immunoglobulin antibody conjugated with a labeling substance, which is commonly an enzyme-labeled antibody, is used. Standard samples containing Crtac1B at various known concentrations are subjected to electrophoretic separation together with a test sample, and transferred onto a membrane. The primary antibody and the labeled secondary antibody are sequentially allowed to react with the transferred samples, and the membrane is then washed, followed by, in cases where the labeling substance is an enzyme, allowing the samples to react with an appropriate substrate, to detect the band. The intensity of the band on the membrane can be digitized using a commercially available image analyzer or the like. Crtac1B in the test sample can be quantified by preparing a calibration curve based on the band intensities of the standard samples, and applying the band intensity of the test sample to this calibration curve.

As concretely described in the Examples below, in patients with relapse of a neurological disease accompanied by at least one of inflammation and demyelination, such as multiple sclerosis, the Crtac1B protein level is significantly lower than in patients without relapse (patients in whom the disease was cured or remitted after definitive diagnosis and no relapse was found thereafter) and the normal control, and the Crtac1B protein levels in the patients without relapse are equivalent to those in the normal control. Therefore, by using a low value of the Crtac1B protein level as an indicator, the presence (initial onset or relapse) of a neurological disease accompanied by at least one of inflammation and demyelination can be detected. In the Examples described below, a significant difference in the Crtac1B protein level was found between patients with relapse of multiple sclerosis or neuromyelitis optica and the normal control. Since patients with relapse are those in whom the disease is once cured or remitted and a lesion newly occurs thereafter, there is no fundamental difference between patients with relapse and patients with initial onset. Therefore, the method of the present invention enables detection of not only relapse but also initial onset cases of the neurological disease accompanied by at least one of inflammation and demyelination. Even in the case where the presence of the disease cannot be clearly determined from clinical symptoms and findings by objective tests such as MRI, onset (initial onset) or relapse of the neurological disease accompanied by at least one of inflammation and demyelination in a subject can be judged to be highly likely when the value of the Crtac1B protein level in a sample derived from the subject is lower than the value in the healthy individuals, so that initiation of therapeutic treatment can be positively considered. The facts that patients who are just suffering from a neurological disease accompanied by at least one of inflammation and demyelination show low values of the Crtac1B protein level, and that the Crtac1B protein level in patients whose disease has been cured or remitted returns to the same level as in the normal control, indicate that monitoring of the progress of, or a therapeutic effect on, the neurological disease can also be carried out based on the Crtac1B protein level. Thus, the method of the present invention can also be used for monitoring the progress of, or a therapeutic effect on, a neurological disease accompanied by at least one of inflammation and demyelination.

In the present invention, the "low value of Crtac1B protein level" means that the measured value of the Crtac1B protein level in the subject sample is significantly lower than the mean value of the Crtac1B protein levels in samples from a population of healthy individuals free of the neurological disease accompanied by at least one of inflammation and demyelination. In the judgment on whether the value is low or not, a cut-off value of the Crtac1B protein level may be set in advance, and the cut-off value may be compared with the measured value of the Crtac1B protein level. In cases where the measured value is below the cut-off value, the patient can be judged to be suffering from the neurological disease accompanied by at least one of inflammation and demyelination.

Those skilled in the art can appropriately determine the cut-off value by a routine survey. More specifically, for example, a plurality of samples (preferably as many samples as possible) are obtained from a group of known patients and a healthy group, and the Crtac1B protein level in each sample is measured to provide a value with which the groups can be distinguished from each other at a desired sensitivity or specificity as a cut-off value. Still more specifically, in general, an ROC curve is generated from the Crtac1B protein concentrations in a plurality of samples derived from both groups, and the point which is most distant from the ROC curve having the lowest prediction/diagnostic performance, that is, most distant from the oblique dotted line corresponding to AUC=0.500, or the point which is closest to the point where the sensitivity is 100% and the false positivity is 0%, is selected as a cut-off value.

In some cases, depending on the type and purpose of the test, a cut-off value having a low specificity but a high sensitivity is selected, or a cut-off value having a high specificity is preferentially selected. In the present invention, the cut-off value may be set such that the sensitivity and the specificity both become high in a good balance, or such that the correct answer can be obtained at the highest rate.

The meanings of the sensitivity and the specificity are the same as the meanings well known in the field of diagnosis. For example, according to the table shown below, the sensitivity is a/(a+b), and the specificity is d/(c+d). The correct answer rate is (a+d)/(a+b+c+d).

TABLE 1

| | Test result | | |
|---|---|---|---|
| | + | − | Total |
| + (With disease) | a (True positive) | b (False negative) | a + b |
| − (Without disease) | c (False positive) | d (True negative) | c + d |
| Total | a + c | b + d | a + b + c + d |

The cut-off value used in the present invention can be a value between 0.6 and 0.8, for example, about 0.7, in terms of the relative concentration with respect to the mean value of the Crtac1B protein concentrations in the samples derived from the normal control group, which is taken as 1. In terms of the absolute concentration, the cut-off value can be a value between 11.5 µg/dL and 16.0 µg/dL, for example, about 13.7 µg/dL. In cases where such a value is employed as the cut-off value, neurological diseases accompanied by at least one of inflammation and demyelination, including multiple sclerosis, can be detected at a favorable sensitivity and specificity.

However, the cut-off value is not limited to the above-described value, and may be set depending on the type and purpose of the test, as mentioned above. In cases where priority should be given to prevention of overlooking of patients, the cut-off value may be set to a higher value, while in cases where priority should be given to reduction of false positivity, the cut-off value may be set to a lower value. For example, in cases where the cut-off value is set to a value between 8.7 µg/dL and 12.0 µg/dL (for example, about 10.23

μg/dL), the possibility of misdiagnosis in which a subject free of the neurological disease accompanied by at least one of inflammation and demyelination or a patient in remission is diagnosed with the disease can be decreased.

The cut-off value most suitable for a certain purpose may vary depending on the population size, race, and the like. The above specific examples of the cut-off value are values obtained as a result of a survey on several ten Japanese patients (see the Examples below). Those skilled in the art can set a suitable cut-off value by the common procedure described herein in detail. Accordingly, cut-off values that may be used in the present invention are not limited to the specific examples of the cut-off value described herein.

EXAMPLES

The present invention is described below more concretely by way of Examples. However, the present invention is not limited to the following Examples.

Samples

Cases who were diagnosed with multiple sclerosis (MS) in Yokohama City University Hospital or the like and regularly attending a hospital were subjected to the analysis. The patients diagnosed with MS were judged according to the McDonald's criteria, which were the international standard, based on objective findings in mainly clinical symptoms and MRI. In cases where representative findings of MS were found twice or more in a patient, the patient was definitively diagnosed with MS. According to the later-mentioned criteria for relapse, a total of 65 cases of MS patients were classified into 3 groups, relapse (35 cases), possible relapse (20 cases), and relapse-free (10 cases). A cerebrospinal fluid (CSF) sample was collected from each case.

As non-MS disease cases, cases who were diagnosed with neuromyelitis optica (NMO) or an NMO spectrum disorder in Yokohama City University Hospital or the like and regularly attending a hospital were subjected to the analysis. The patients diagnosed with NMO were judged according to the criteria which were proposed by Wingerchuk et al. and widely employed (Wingerchuk, D. M., V. A. Lennon, et al. (2006). "Revised diagnostic criteria for neuromyelitis optica." Neurology 66(10): 1485-1489). It has been thought that, even in cases not satisfying the above criteria, a disease state similar to NMO can be considered to be present if the presence of an anti-aquaporin 4 antibody (anti-AQP4 antibody) has been found even once in serum of the patient. Such cases are called NMO spectrum disorder, and treated in the same manner as cases of NMO. In the present study, NMO spectrum disorder was regarded as the same disease state as NMO, and NMO and NMO spectrum disorder were included in the analysis. According to the later-mentioned criteria for relapse, a total of 20 cases of NMO patients (including NMO spectrum disorder patients) were classified into 3 groups, relapse (13 cases), possible relapse (4 cases), and relapse-free (3 cases). A cerebrospinal fluid (CSF) sample was collected from each case.

As cases of further additional diseases, 10 cases of Guillain-Barré syndrome (GBS), 6 cases of chronic inflammatory demyelinating polyneuropathy (CIDP), 12 cases of meningitis/meningoencephalitis, and 4 cases of neurosarcoidosis were subjected to collection of cerebrospinal fluid samples. As disease controls, 22 cases of amyotrophic lateral sclerosis (ALS) and 10 cases of multiple system atrophy (MSA), and, as a normal control, 29 cases of individuals free of neurological diseases, were subjected to collection of cerebrospinal fluid samples.

Diagnosis of relapse in the MS and NMO patients was carried out as follows.

(1) Each patient was examined by a physician, and the presence or absence of relapse was judged based on the medical history, examination and clinical findings. Patients diagnosed as having relapse were classified as "clinical relapse", and patients diagnosed as relapse-free were classified as "no clinical relapse (remission)"

(2) Subsequently, tests capable of objective confirmation of the presence or absence of relapse (contrast-enhanced MRI, plain MRI, electrophysiological examination, and ophthalmologic examination) were carried out, if necessary. As the electrophysiological examination, measurement of the visual evoked potential (VEP), somatosensory evoked potential (SEP), and motor evoked potential (MEP) was carried out.

(3) Among the patients diagnosed as having "clinical relapse", those in whom relapse was also found in the tests were classified as definite relapse. Among the patients diagnosed as having "clinical relapse", those in whom no relapse was found in the tests were classified as possible relapse (this patient group may include patients actually having relapse and patients free of relapse). Among the patients diagnosed as having "no clinical relapse", those in whom relapse was also not found in the tests were classified as no relapse. None of the patients diagnosed as having "no clinical relapse" was found to have relapse in the tests.

Western Blotting

Proteins in the samples were separated by SDS-PAGE using 6% polyacrylamide gel, and Crtac1B (hereinafter also referred to as LOTUS) was detected by Western blotting. The antibody to be used as the primary antibody was prepared by the ordinary hybridoma method using as an immunogen the region corresponding to the 516th-546th amino acids in mouse LOTUS (SEQ ID NO:3). As the secondary antibody, a rabbit labeled anti-human IgG antibody (HRP-conjugated anti-rabbit antibody, NA934, manufactured by GE Healthcare) was used. The band having a molecular weight of 70 kD was detected as the band of Crtac1B.

A calibration curve for quantification of the Crtac1B concentration in each sample was made as follows. Human Crtac1B was purified from cultured cells using a molecular biological method. The concentration of the purified human Crtac1B sample was measured, and 4 kinds of samples for the calibration curve were prepared by serial dilution to appropriate concentrations. In SDS-PAGE of cerebrospinal fluid samples, the 4 kinds of diluted samples were also loaded on the same gel, and subjected to Western blotting (FIG. 1, $a$). The intensities of the bands of Crtac1B were measured (FIG. 1, $b$), and the correlation between the concentrations of the 4 kinds of samples for the calibration curve and the measured intensities of the bands was plotted to obtain a calibration curve (FIG. 1, $c$).

The intensity of the Crtac1B band of each sample subjected to the electrophoresis on the same gel was measured, and applied to the calibration curve to calculate the Crtac1B concentration (mmol/L) in the sample. The unit was converted to g/dl, which is a unit commonly used for representing the protein concentration in a spinal fluid, to provide the result of the concentration measurement. Based on the result, an ROC curve was prepared.

Results

Figure 2:
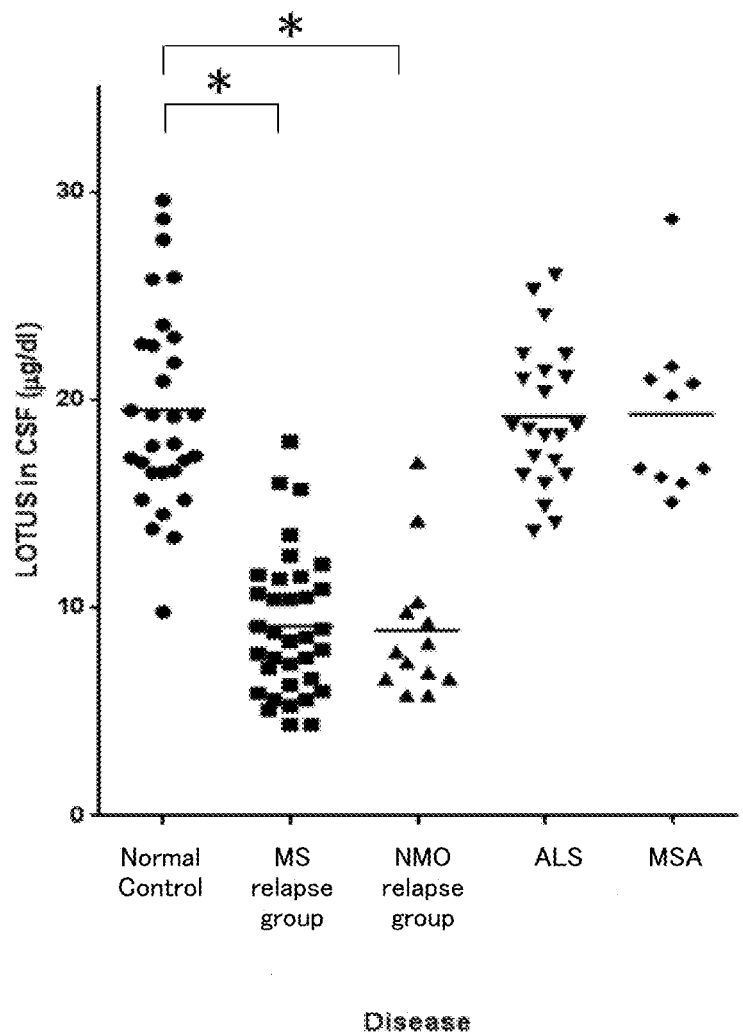
FIG. 2 is a scatter diagram showing the results of measurement of the Crtac1B (LOTUS) protein concentration in cerebrospinal fluid samples derived from the normal control group and disease groups. MS, multiple sclerosis; NMO, neuromyelitis optica; ALS, amyotrophic lateral sclerosis; MSA, multiple system atrophy. * indicates significant difference at P<0.05.
Figure 3:
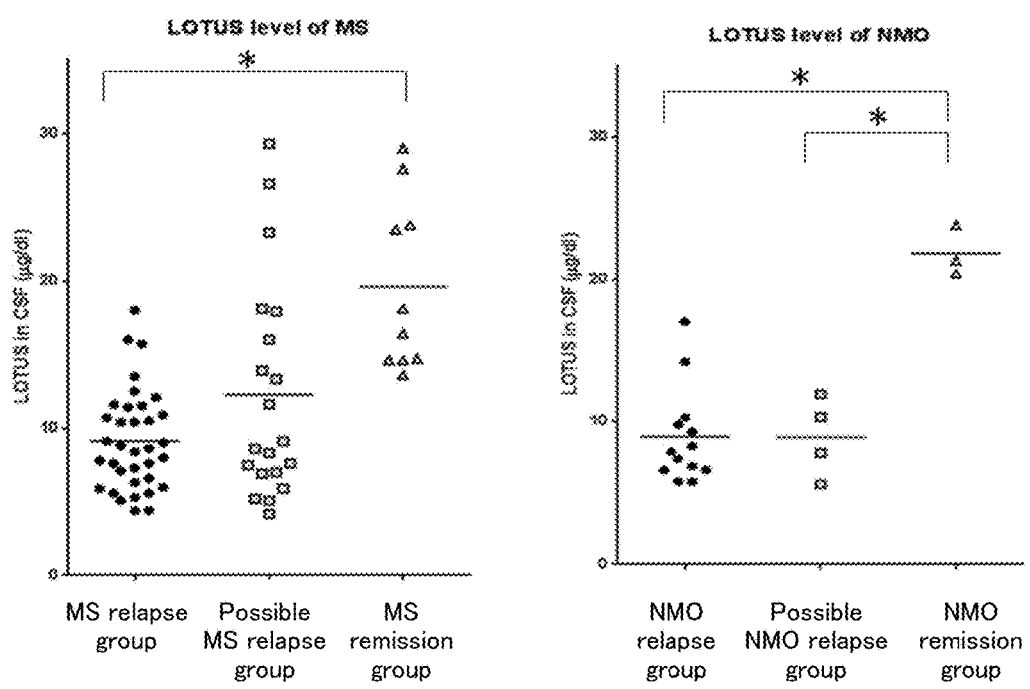
FIG. 3 shows scatter diagrams showing the results of measurement of the Crtac1B (LOTUS) protein concentration in cerebrospinal fluid samples from a relapse group, possible relapse group, and relapse-free (remission) group of multiple sclerosis (MS) and neuromyelitis optica (NMO). * indicates significant difference at P<0.05.
Figure 4:
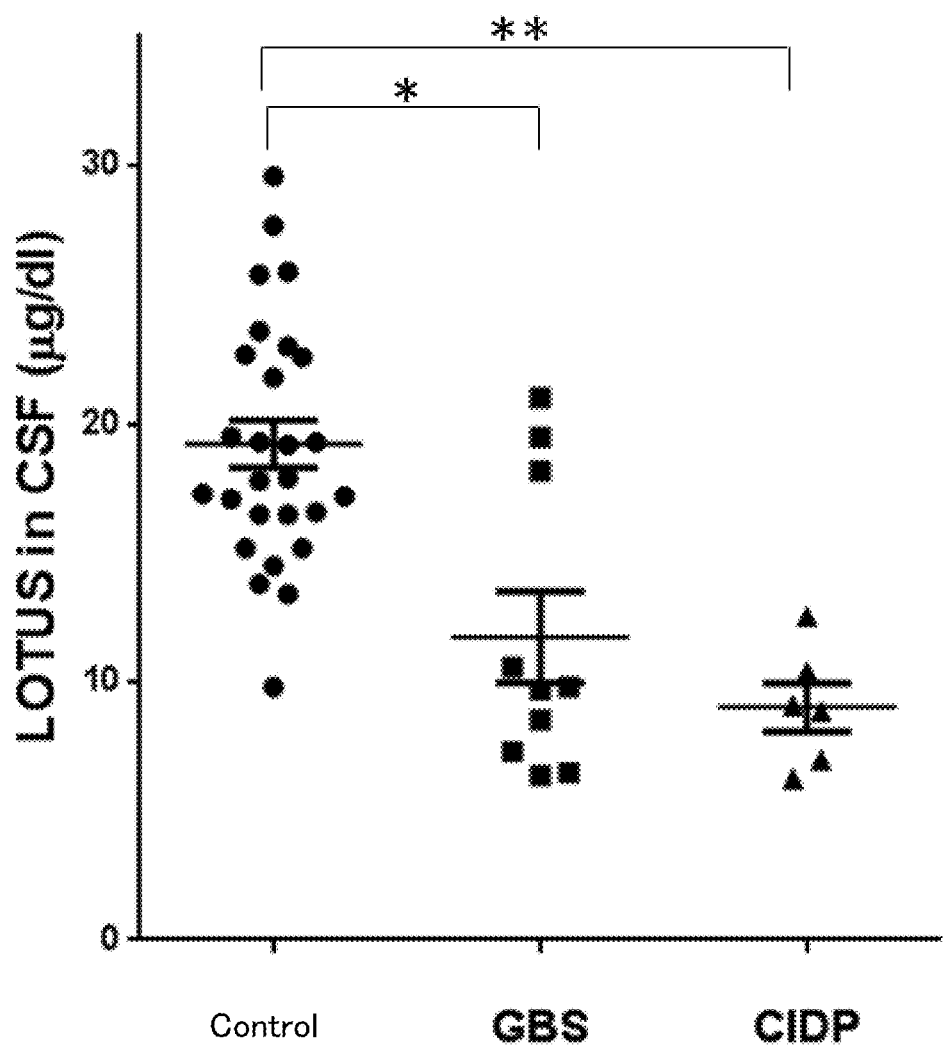
FIG. 4 is a scatter diagram showing the results of measurement of the Crtac1B (LOTUS) protein concentration in cerebrospinal fluid samples derived from the normal control group, Guillain-Barré syndrome (GBS) patient group, and chronic inflammatory demyelinating polyneuropathy (CIDP) patient group. * indicates significant difference at P<0.05. ** indicates significant difference at P<0.01.
Figure 5:
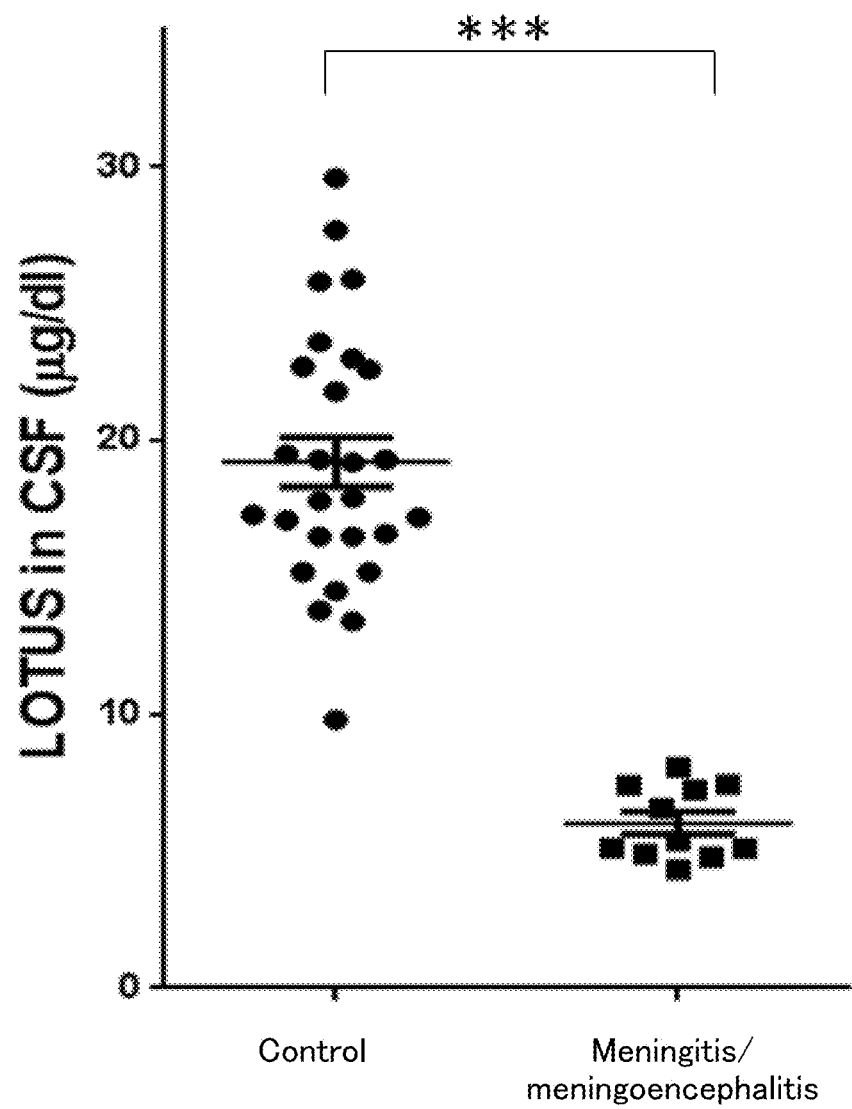
FIG. 5 is a scatter diagram showing the results of measurement of the Crtac1B (LOTUS) protein concentration in cerebrospinal fluid samples derived from the normal control group and meningitis/meningoencephalitis patient group. *** indicates significant difference at P<0.0001.
Figure 6:
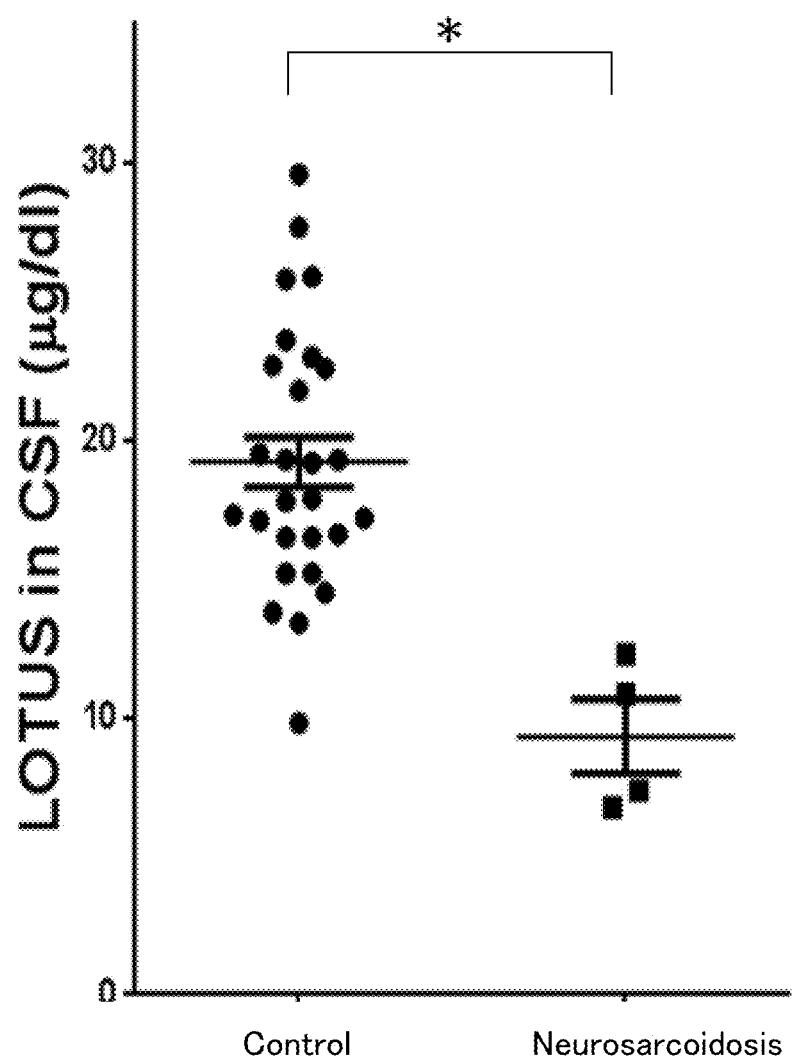
FIG. 6 is a scatter diagram showing the results of measurement of the Crtac1B (LOTUS) protein concentration in cerebrospinal fluid samples derived from the normal control group and neurosarcoidosis patient group. * indicates significant difference at P<0.05.

In the normal control group, the mean value of the LOTUS concentration in the cerebrospinal fluid was 19.21 µg/dl. On the other hand, in the MS relapse group, the mean value was 9.13 µg/dl. Thus, a decrease in the concentration by about 50% was found in the patients with relapse of MS (FIG. 2). ALS and MSA are diseases classified into the neurodegenerative diseases, and accompanied by neither inflammation nor demyelination. In these diseases, the LOTUS concentration in the sample did not decrease, and was at the same level as that in the normal control (FIG. 2). As a result of investigation of the LOTUS concentration in the cerebrospinal fluid in each of the possible MS relapse group and the MS no-relapse group, the patients diagnosed as having no relapse of MS (remission) were found to have LOTUS concentrations as high as those in the normal control group, as shown in FIG. 3. The MS possible relapse group is considered to contain both patients with relapse of MS and patients with no relapse of MS. Since the LOTUS concentration largely varied in the possible relapse group, it was suggested that the presence or absence of relapse in each patient in the MS possible relapse group could be determined according to the LOTUS concentration.

The sensitivity and specificity of differential diagnosis based on the ROC curve between the MS relapse group and the normal control group were as shown in the Table 2 below. Each cut-off value was represented as the relative concentration and absolute concentration (shown in parentheses).

TABLE 2

| Cut-off value | Number of true-positive cases of MS | Number of false-negative cases of MS | Number of false-positive cases of MS | Number of true-negative cases of MS | Sensitivity (%) | Specificity (%) | Correct answer rate (%) |
| --- | --- | --- | --- | --- | --- | --- | --- |
| 0.525 (10.08 µg/dl) | 21 | 14 | 1 | 26 | 60.0 | 96.30 | 75.81 |
| 0.601 (11.55 µg/dl) | 28 | 7 | 1 | 26 | 80.0 | 96.30 | 87.10 |
| 0.711 (13.65 µg/dl) | 32 | 3 | 2 | 25 | 91.43 | 92.59 | 93.55 |
| 0.825 (15.85 µg/dl) | 33 | 2 | 6 | 21 | 94.29 | 77.78 | 87.10 |
| 0.913 (17.55 µg/dl) | 34 | 1 | 12 | 15 | 97.14 | 55.56 | 79.03 |

MS: Multiple sclerosis

The LOTUS concentration was similarly investigated in the samples from the cases of NMO relapse, and cases of GBS, CIDP, meningitis/meningoencephalitis, and neurosarcoidosis. As a result, decreases in the LOTUS concentration were observed similarly to the MS relapse cases (FIGS. 2 to 6). FIG. 3 shows the result of investigation of the LOTUS concentration in each sample in the possible-relapse group and relapse-free (remission) group of NMO cases. It can be said that all the 4 cases diagnosed with possible relapse of NMO are highly likely to be suffering from relapse of NMO based on the LOTUS concentration.

Table 3 shows the sensitivity and specificity of differential diagnosis based on the ROC curve between the GBS group and the normal control group; Table 4 shows the sensitivity and specificity of differential diagnosis between the CIDP group and the normal control group; Table 5 shows the sensitivity and specificity of differential diagnosis between the meningitis/meningoencephalitis group and the normal control group; and Table 6 shows the sensitivity and specificity of differential diagnosis between the neurosarcoidosis group and the normal control group (the cut-off values are represented as the relative concentration).

TABLE 3

| Cut-off value | Number of true-positive cases of GBS | Number of false-negative cases of GBS | Number of false-positive cases of GBS | Number of true-negative cases of GBS | Sensitivity (%) | Specificity (%) | Correct answer rate (%) |
| --- | --- | --- | --- | --- | --- | --- | --- |
| 0.5075 | 6 | 4 | 0 | 29 | 60 | 100 | 89.7 |
| 0.6187 | 7 | 3 | 1 | 28 | 70 | 96.55 | 89.7 |
| 0.7020 | 7 | 3 | 2 | 27 | 70 | 93.10 | 87.2 |
| 0.8217 | 7 | 3 | 6 | 23 | 70 | 79.31 | 76.9 |
| 0.9070 | 7 | 3 | 13 | 16 | 70 | 55.17 | 60.0 |

GBS: Guillain-Barré syndrome

TABLE 4

| Cut-off value | Number of true-positive cases of CIDP | Number of false-negative cases of CIDP | Number of false-positive cases of CIDP | Number of true-negative cases of CIDP | Sensitivity (%) | Specificity (%) | Correct answer rate (%) |
|---|---|---|---|---|---|---|---|
| 0.4892 | 4 | 2 | 0 | 29 | 66.67 | 100 | 94.3 |
| 0.5932 | 5 | 1 | 1 | 28 | 83.33 | 96.55 | 94.3 |
| 0.7020 | 6 | 0 | 2 | 27 | 100 | 93.10 | 94.3 |
| 0.7874 | 6 | 0 | 5 | 24 | 100 | 82.76 | 85.7 |
| 0.9070 | 6 | 0 | 13 | 16 | 100 | 55.17 | 62.9 |

CIDP: Chronic inflammatory demyelinating polyneuropathy

TABLE 5

| Cut-off value | Number of true-positive cases of meningitis/meningoencephalitis | Number of false-negative cases of meningitis/meningoencephalitis | Number of false-positive cases of meningitis/meningoencephalitis | Number of true-negative cases of meningitis/meningoencephalitis | Sensitivity (%) | Specificity (%) | Correct answer rate (%) |
|---|---|---|---|---|---|---|---|
| 0.4963 | 8 | 4 | 0 | 29 | 66.67 | 100 | 90.24 |
| 0.5425 | 9 | 3 | 1 | 28 | 75 | 96.55 | 90.24 |
| 0.6437 | 12 | 0 | 1 | 28 | 100 | 96.55 | 97.56 |
| 0.7020 | 12 | 0 | 2 | 27 | 100 | 93.1 | 95.12 |

TABLE 6

| Cut-off value | Number of true-positive cases of Sarc | Number of false-negative cases of Sarc | Number of false-positive cases of Sarc | Number of true-negative cases of Sarc | Sensitivity (%) | Specificity (%) | Correct answer rate (%) |
|---|---|---|---|---|---|---|---|
| 0.446 | 2 | 2 | 0 | 27 | 50 | 100 | 93.54 |
| 0.602 | 3 | 1 | 1 | 26 | 75 | 96.30 | 93.54 |
| 0.668 | 4 | 0 | 1 | 26 | 100 | 96.30 | 96.77 |
| 0.708 | 4 | 0 | 2 | 25 | 100 | 92.59 | 93.54 |

Sarc: Neurosarcoidosis

The biomarker of the present invention was compared with existing biomarkers (IgG index, oligoclonal band (OCB), and myelin basic protein (MBP)). The results are shown in Table 7 and Table 8 below. OCB was detected by isoelectric focusing of cerebrospinal fluid, and each sample was judged as positive when 2 or more bands appeared in the γ-globulin region. In terms of MBP, each sample was judged as positive when the concentration was 31.2 pg/ml or more.

The study was carried out using two types of cut-off values of LOTUS, and both values produced better diagnostic results than the existing biomarkers. With a cut-off value of LOTUS of 13.7, cases of relapse of MS could be diagnosed at a very high diagnostic rate. With a cut-off value of LOTUS of 12.0, the diagnostic rate of cases of relapse of MS slightly decreased, but misdiagnosis in cases of remission without relapse and the normal control could be kept lower.

TABLE 7

|  | Normal control | MS relapse | NMO relapse | MSA | ALS |
|---|---|---|---|---|---|
| n | 30 | 35 | 13 | 10 | 22 |
| Age | 47.6 ± 21.8 | 35.9 ± 11.2 | 45.2 ± 16.2 | 65.1 ± 9.3 | 68.2 ± 12.2 |
| Sex | Male 56.7% Female 43.3% | Male 28.6% Female 71.4% | Male 15.4% Female 84.6% | Male 70% Female 30% | Male 59.1% Female 40.9% |
| Mean of IgG index | 0.65 ± 0.23 | 0.93 ± 0.35 | 0.83 ± 0.32 | 0.66 ± 0.07 | 0.59 ± 0.16 |
| Positive rate of IgG index (>0.73) | 23% (6/26) | 62.9% (22/35) | 53.8% (7/13) | 33% (3/10) | 27.2% (6/22) |
| Positive rate of OCB | 0% (0/14) | 54.5% (18/33) | 23.1% (3/13) | 0 | 0 |
| Positive rate of MBP | 0% (0/14) | 47.1% (16/34) | 58.3% (7/12) | 0 | 0 |
| Positive rate of LOTUS (<12.0) | 3.3% (1/30) | 82.9% (29/35) | 84.6% (11/13) | 0 | 0 |
| Positive rate of LOTUS (<13.7) | 6.6% (2/30) | 91.4% (32/35) | 84.6% (11/13) | 0 | 0 |

TABLE 8

|  | MS relapse | Possible MS | No relapse of MS |
|---|---|---|---|
| n | 35 | 20 | 10 |
| Age | 35.9 ± 11.2 | 42.9 ± 11.1 | 37.9 ± 14.7 |
| EDSS | 3.0 ± 1.8 | 2.2 ± 1.5 | 2.0 ± 1.7 |
| CSF protein (mg/dl) | 29.9 ± 10.1 | 34.9 ± 12.5 | 35.9 ± 15.4 |
| Mean of IgG index | 0.93 ± 0.35 | 0.83 ± 0.40 | 0.77 ± 0.21 |
| Positive rate of IgG index (>0.73) | 63.6% (21/33) | 36.8% (6/19) | 30.0% (3/10) |
| Positive rate of OCB | 62.9% (22/35) | 29.4% (5/17) | 25.0% (2/8) |
| Positive rate of MBP | 47.1% (16/34) | 36.8% (7/19) | 11.1% (1/9) |
| Mean of LOTUS (μg/dl) | 9.1 ± 3.4 | 12.3 ± 7.4 | 19.6 ± 5.8 |
| Positive rate of LOTUS (<12.0) | 82.9% (29/35) | 60.0% (12/20) | 0.0% (0/10) |
| Positive rate of LOTUS (<13.7) | 91.4% (32/35) | 65.0% (13/20) | 10.0% (1/10) |

The invention claimed is:

1. A method for detecting cartilage acidic protein 1B (Crtac1B), said method comprising:
   measuring a level of Crtac1B protein in a sample separated from a human subject with neurological disease excluding cerebral infarction by an immunoassay using a non-human animal antibody that binds to Crtac1B protein.

2. The method according to claim 1, wherein said neurological disease excluding cerebral infarction is at least one selected from the group consisting of demyelinating disease in central nervous system, inflammatory disease in central nervous system, peripheral demyelinating neuropathy, and acute central nervous system disorders complicating autoimmune disease.

3. The method according to claim 1, wherein said neurological disease excluding cerebral infarction is at least one selected from the group consisting of multiple sclerosis, neuromyelitis optica, Guillain-Barré syndrome, chronic inflammatory demyelinating polyneuropathy, meningitis, meningoencephalitis, encephalitis, encephalopathy, and neurosarcoidosis.

4. The method according to claim 1, wherein said neurological disease excluding cerebral infarction is at least one selected from the group consisting of multiple sclerosis, neuromyelitis optica, Guillain-Barré syndrome, chronic inflammatory demyelinating polyneuropathy, meningitis, and meningoencephalitis.

5. The method as in any of claims 1 or 2-4, wherein said sample is blood or cerebrospinal fluid.

6. A method for detecting cartilage acidic protein 1B (Crtac1B) protein in a human patient with neurological disease excluding cerebral infarction, said method comprising:
   detecting Crtac1B protein in a sample separated from the human patient with neurological disease excluding cerebral infarction by separating proteins comprising cartilage acidic protein 1A (Crtac1A) and cartilage acidic protein 1B (Crtac1B) contained in the sample and a molecular marker by electrophoresis;
   contacting the separated proteins with a primary antibody that binds to both Crtac1A protein and Crtac1B protein and thereafter with a labeled second antibody; and then
   detecting Crtac1B protein at position 70 kD according to the molecular weight marker.

7. The method according to claim 6, wherein said sample is blood or cerebrospinal fluid.

8. A method for detecting cartilage acidic protein 1B (Crtac1B) protein in a patient with a neurological disease excluding cerebral infarction, said method comprising:
   detecting Crtac1B protein in a sample separated from the patient with neurological disease excluding cerebral infarction by contacting the sample with an anti-Crtac1B antibody that selectively binds to the Crtac1B protein, but does not bind to Crtac1A protein, and detecting binding between Crtac1B protein and the antibody.

9. The method according to claim 8, wherein the anti-Crtac1B antibody selectively binds to the C-terminal region corresponding of 607th to 645th amino acids in Crtac1B (SEQ ID NO:2).

10. The method according to claim 8, wherein said sample is blood or cerebrospinal fluid.

* * * * *